United States Patent
Bourg, Jr.

(10) Patent No.: US 8,158,175 B2
(45) Date of Patent: Apr. 17, 2012

(54) METHOD FOR REAL TIME MEASUREMENT OF ACRYLAMIDE IN A FOOD PRODUCT

(75) Inventor: Wilfred Marcellien Bourg, Jr., Melissa, TX (US)

(73) Assignee: Frito-Lay North America, Inc., Plano, TX (US)

( * ) Notice: Subject to any disclaimer, the term of this patent is extended or adjusted under 35 U.S.C. 154(b) by 348 days.

(21) Appl. No.: 12/545,574

(22) Filed: Aug. 21, 2009

(65) Prior Publication Data

US 2010/0055259 A1    Mar. 4, 2010

Related U.S. Application Data

(60) Provisional application No. 61/092,513, filed on Aug. 28, 2008.

(51) Int. Cl.
*A23L 1/01*    (2006.01)

(52) U.S. Cl. ........ 426/233; 426/438; 426/465; 426/523; 700/208; 700/211

(58) Field of Classification Search .......... 426/231–233, 426/523, 465, 248, 438; 700/208, 211; 348/89
See application file for complete search history.

(56) References Cited

U.S. PATENT DOCUMENTS

| | | | |
|---|---|---|---|
| 1,053 A | 12/1838 | Hatfield |
| 1,782,960 A | 11/1930 | Erysin |
| 2,448,152 A | 8/1948 | Patton |
| 2,490,431 A | 12/1949 | Greene |
| 2,498,024 A | 2/1950 | Baxter |
| 2,584,893 A | 2/1952 | Lloyd |
| 2,611,705 A | 9/1952 | Hendel |
| 2,704,257 A | 3/1955 | deSellano |
| 2,744,017 A | 5/1956 | Baldwin |
| 2,759,832 A | 8/1956 | Cording, Jr. |
| 2,762,709 A | 9/1956 | Janis |
| 2,780,552 A | 2/1957 | Willard |
| 2,893,878 A | 7/1959 | Simon |
| 2,905,559 A | 9/1959 | Anderson |
| 2,910,367 A | 10/1959 | Melnick |
| 2,987,401 A | 6/1961 | Johnston |
| 3,026,885 A | 3/1962 | Eytinge |
| 3,027,258 A | 3/1962 | Markakis |
| 3,038,810 A | 6/1962 | Akerboom |

(Continued)

FOREIGN PATENT DOCUMENTS

CL    4032002    6/2003

(Continued)

OTHER PUBLICATIONS

Health Canada Food & Nutrition "Acrylamide and Food" Dec. 1, 2005 (3 pages).

(Continued)

*Primary Examiner* — Drew E Becker
(74) *Attorney, Agent, or Firm* — James R. Gourley; Bobby W. Braxton; Carstens & Cahoon, LLP

(57) ABSTRACT

Disclosed is a method for the real time measurement of acrylamide in a food product. Wavelength emission data is collected from a food product. The same food product is tested off-line in an analytical laboratory for levels of acrylamide pre-cursors or acrylamide. The wavelength emission data is then correlated with the off-line laboratory data.

19 Claims, 4 Drawing Sheets

U.S. PATENT DOCUMENTS

| | | |
|---|---|---|
| 3,044,880 A | 7/1962 | Bogyo |
| 3,085,020 A | 4/1963 | Backinger |
| 3,219,458 A | 11/1965 | Higby |
| 3,278,311 A | 10/1966 | Brown |
| 3,305,366 A | 2/1967 | Sutton |
| 3,359,123 A | 12/1967 | Katucki |
| 3,365,301 A | 1/1968 | Lipoma |
| 3,369,908 A | 2/1968 | Gonzalez |
| 3,370,627 A | 2/1968 | Willard |
| 3,404,986 A | 10/1968 | Wimmer |
| 3,436,229 A | 4/1969 | Simpson |
| 3,460,162 A | 8/1969 | Sijbring |
| 3,545,979 A | 12/1970 | Ghafoori |
| 3,578,463 A | 5/1971 | Smith |
| 3,608,728 A | 9/1971 | Trimble |
| 3,620,925 A | 11/1971 | Mochizuki |
| 3,627,535 A | 12/1971 | Davidson |
| 3,634,095 A | 1/1972 | Willard |
| 3,652,402 A | 3/1972 | Chibata |
| 3,687,679 A | 8/1972 | Sijbring |
| 3,690,895 A | 9/1972 | Amadon |
| 3,725,087 A | 4/1973 | Miller |
| 3,773,624 A | 11/1973 | Wagner |
| 3,782,973 A | 1/1974 | Pittet |
| 3,812,775 A | 5/1974 | Sijbring |
| 3,849,582 A | 11/1974 | Blagdon |
| 3,851,572 A | 12/1974 | Lazzarini |
| 3,870,809 A | 3/1975 | Green |
| 3,914,436 A | 10/1975 | Nakadai |
| 3,917,866 A | 11/1975 | Purves |
| 3,925,568 A | 12/1975 | Rao |
| 3,987,210 A | 10/1976 | Cremer |
| 3,997,684 A | 12/1976 | Willard |
| 3,998,975 A | 12/1976 | Liepa |
| 4,005,225 A | 1/1977 | Craig |
| 4,073,952 A | 2/1978 | Standing |
| 4,084,008 A | 4/1978 | Yueh |
| 4,122,198 A | 10/1978 | Wisdom |
| 4,124,727 A | 11/1978 | Rockland |
| 4,136,208 A | 1/1979 | Light |
| 4,140,801 A | 2/1979 | Hilton |
| 4,167,137 A | 9/1979 | van Remmen |
| 4,192,773 A | 3/1980 | Yoshikawa |
| 4,199,612 A | 4/1980 | Fragas |
| 4,210,594 A | 7/1980 | Logan |
| 4,251,895 A | 2/1981 | Caridis |
| 4,272,554 A | 6/1981 | Schroeder |
| 4,277,510 A | 7/1981 | Wicklund |
| 4,312,892 A | 1/1982 | Rubio |
| 4,317,742 A | 3/1982 | Yamaji |
| 4,394,398 A | 7/1983 | Wilson |
| 4,418,088 A | 11/1983 | Cantenot |
| 4,461,832 A | 7/1984 | Tschang |
| 4,537,786 A | 8/1985 | Bernard |
| 4,555,409 A | 11/1985 | Hart |
| 4,582,927 A | 4/1986 | Fulcher |
| 4,594,260 A | 6/1986 | Vaquerio |
| 4,595,597 A | 6/1986 | Lenchin |
| 4,645,679 A | 2/1987 | Lee |
| 4,673,581 A | 6/1987 | Fulcher |
| 4,706,556 A | 11/1987 | Wallace |
| 4,721,625 A | 1/1988 | Lee |
| 4,749,579 A | 6/1988 | Haydock |
| 4,751,093 A | 6/1988 | Hong |
| 4,756,916 A | 7/1988 | Dreher |
| 4,806,377 A | 2/1989 | Ellis |
| 4,844,930 A | 7/1989 | Mottur |
| 4,844,931 A | 7/1989 | Webb |
| 4,863,750 A | 9/1989 | Pawlak |
| 4,884,780 A | 12/1989 | Ohashi |
| 4,889,733 A | 12/1989 | Willard |
| 4,900,576 A | 2/1990 | Bonnett |
| 4,917,909 A | 4/1990 | Prosise |
| 4,931,296 A | 6/1990 | Shanbhag |
| 4,933,199 A | 6/1990 | Neel |
| 4,937,085 A | 6/1990 | Cherry |
| 4,963,373 A | 10/1990 | Fan |
| 4,966,782 A | 10/1990 | Heidolph |
| 4,971,813 A | 11/1990 | Strobel |
| 4,978,684 A | 12/1990 | Cerami |
| 4,985,269 A | 1/1991 | Irvin |
| 5,002,784 A | 3/1991 | Pare |
| 5,009,903 A | 4/1991 | deFigueiredo |
| 5,035,904 A | 7/1991 | Huang |
| 5,045,335 A | 9/1991 | DeRooij |
| 5,071,661 A | 12/1991 | Stubbs |
| 5,087,467 A | 2/1992 | Schwank |
| 5,126,153 A | 6/1992 | Beck |
| 5,134,263 A | 7/1992 | Smith |
| 5,167,975 A | 12/1992 | Tsurumaki |
| 5,171,600 A | 12/1992 | Young |
| 5,176,933 A | 1/1993 | Fulcher |
| 5,196,225 A | 3/1993 | Lush |
| 5,232,721 A | 8/1993 | Polansky |
| 5,279,840 A | 1/1994 | Baisier |
| 5,292,542 A | 3/1994 | Beck |
| 5,298,274 A | 3/1994 | Khalsa |
| 5,356,646 A | 10/1994 | Simic-Glavaski |
| 5,362,511 A | 11/1994 | Villagran |
| 5,368,879 A | 11/1994 | White |
| 5,370,898 A | 12/1994 | Zussman |
| 5,389,389 A | 2/1995 | Beck |
| 5,391,384 A | 2/1995 | Mazza |
| 5,391,385 A | 2/1995 | Seybold |
| 5,393,543 A | 2/1995 | Laufer |
| 5,394,790 A | 3/1995 | Smith |
| 5,441,758 A | 8/1995 | Lewis |
| 5,447,742 A | 9/1995 | Malvido |
| 5,458,903 A | 10/1995 | Colson |
| 5,464,642 A | 11/1995 | Villagran |
| 5,464,643 A | 11/1995 | Lodge |
| 5,505,978 A | 4/1996 | Roy |
| 5,514,387 A | 5/1996 | Zimmerman |
| 5,534,280 A | 7/1996 | Welch |
| 5,554,405 A | 9/1996 | Fazzolare |
| 5,558,886 A | 9/1996 | Martinez-Bustos |
| 5,589,213 A | 12/1996 | Desai |
| 5,603,972 A | 2/1997 | McFarland |
| 5,603,973 A | 2/1997 | Benson |
| 5,620,727 A | 4/1997 | Gerrish |
| 5,676,042 A | 10/1997 | Sakuma |
| 5,690,982 A | 11/1997 | Fazzolare |
| 5,695,804 A | 12/1997 | Hnat |
| 5,707,671 A | 1/1998 | Beck |
| 5,747,084 A | 5/1998 | Cochran |
| 5,776,531 A | 7/1998 | Aasman |
| 5,792,499 A | 8/1998 | Atwell |
| 5,846,589 A | 12/1998 | Baker |
| 5,858,429 A | 1/1999 | Wallace |
| 5,858,431 A | 1/1999 | Wiedersatz |
| 5,887,073 A | 3/1999 | Fazzari |
| 5,919,691 A | 7/1999 | Schulein |
| 5,945,146 A | 8/1999 | Twinam |
| 5,947,010 A | 9/1999 | Barry |
| 5,972,367 A | 10/1999 | Inoue |
| 5,972,397 A | 10/1999 | Durance |
| 6,001,409 A | 12/1999 | Gimmler |
| 6,016,096 A | 1/2000 | Barnes |
| 6,025,011 A | 2/2000 | Wilkinson |
| 6,033,707 A | 3/2000 | Lanner |
| 6,039,978 A | 3/2000 | Bangs |
| 6,066,353 A | 5/2000 | Villagran |
| 6,068,872 A | 5/2000 | Hashiguchi |
| 6,068,873 A | 5/2000 | Delrue |
| RE36,785 E | 7/2000 | Colson |
| 6,139,884 A | 10/2000 | Shifferaw |
| 6,159,530 A | 12/2000 | Christiansen |
| 6,207,204 B1 | 3/2001 | Christiansen |
| 6,210,720 B1 | 4/2001 | Leusner |
| 6,227,421 B1 | 5/2001 | Richard |
| 6,287,672 B1 | 9/2001 | Fields |
| 6,290,999 B1 | 9/2001 | Gerrish |
| 6,299,914 B1 | 10/2001 | Christiansen |
| 6,335,048 B1 | 1/2002 | Swarvar |
| 6,358,544 B1 | 3/2002 | Henry, Jr. |
| 6,383,533 B1 | 5/2002 | Soeda |
| 6,419,965 B1 | 7/2002 | Douaire |

| | | |
|---|---|---|
| 6,436,458 B2 | 8/2002 | Kuechle |
| 6,521,871 B1 | 2/2003 | Shelton |
| 6,528,768 B1 | 3/2003 | Simic-Glavaski |
| 6,531,174 B2 | 3/2003 | Barrett et al. |
| 6,558,730 B1 | 5/2003 | Gisaw |
| 6,599,547 B1 | 7/2003 | Villagran |
| 6,607,777 B2 | 8/2003 | Walsh |
| 6,638,554 B1 | 10/2003 | Rubio |
| 6,638,558 B2 | 10/2003 | Brubacher |
| 6,716,462 B2 | 4/2004 | Prosise |
| 6,770,469 B2 | 8/2004 | Yamaguchi |
| 6,778,887 B2 | 8/2004 | Britton |
| 6,828,527 B2 | 12/2004 | Simic-Glavaski |
| 6,872,417 B1 | 3/2005 | Freudenrich |
| 6,896,528 B2 | 5/2005 | Kubota |
| 6,929,812 B2 | 8/2005 | Van Der Doe |
| 6,989,167 B2 | 1/2006 | Howie |
| 7,037,540 B2 | 5/2006 | Elder |
| 7,122,719 B2 | 10/2006 | Hakimi |
| 7,169,417 B2 | 1/2007 | Lang |
| 7,189,422 B2 | 3/2007 | Howie |
| 7,190,813 B2 | 3/2007 | Daley |
| 7,220,440 B2 | 5/2007 | Dria |
| 7,267,834 B2 | 9/2007 | Elder |
| 7,291,380 B2 | 11/2007 | Nyholm |
| 7,393,550 B2 | 7/2008 | Barry |
| 7,514,113 B2 | 4/2009 | Zyzak |
| 7,524,519 B2 | 4/2009 | Zyzak |
| 7,527,815 B2 | 5/2009 | Teras |
| 7,534,934 B2 | 5/2009 | Rommens |
| 2002/0018838 A1 | 2/2002 | Zimmerman |
| 2002/0025367 A1 | 2/2002 | Koehler |
| 2002/0129713 A1 | 9/2002 | Caridis |
| 2003/0049359 A1 | 3/2003 | Kulkami |
| 2003/0183092 A1 | 10/2003 | Barber |
| 2003/0198725 A1 | 10/2003 | Cardenas |
| 2003/0219518 A1 | 11/2003 | Li |
| 2004/0047973 A1 | 3/2004 | Bourhis |
| 2004/0086597 A1 | 5/2004 | Awad |
| 2004/0101607 A1 | 5/2004 | Zyzak |
| 2004/0105929 A1 | 6/2004 | Tomoda |
| 2004/0109926 A1 | 6/2004 | Tomoda |
| 2004/0115321 A1 | 6/2004 | Tricoit |
| 2004/0126469 A1 | 7/2004 | Tomoda |
| 2004/0131737 A1 | 7/2004 | Tomoda |
| 2004/0166210 A1* | 8/2004 | Barry et al. ............ 426/243 |
| 2004/0180125 A1 | 9/2004 | Plank |
| 2004/0180129 A1 | 9/2004 | Plank |
| 2004/0197012 A1* | 10/2004 | Bourg et al. ............ 382/110 |
| 2004/0224066 A1 | 11/2004 | Lindsay |
| 2005/0064084 A1 | 3/2005 | Elder |
| 2005/0068535 A1 | 3/2005 | Bond |
| 2005/0074538 A1 | 4/2005 | Elder |
| 2005/0079254 A1 | 4/2005 | Corrigan |
| 2005/0118322 A1 | 6/2005 | Elder |
| 2005/0152811 A1 | 7/2005 | Taylor |
| 2005/0196504 A1 | 9/2005 | Finley |
| 2005/0214411 A1 | 9/2005 | Lindsay |
| 2006/0019007 A1 | 1/2006 | Baas |
| 2006/0029992 A1* | 2/2006 | Grune et al. ............ 435/18 |
| 2006/0043022 A1 | 3/2006 | Wada |
| 2006/0088633 A1 | 4/2006 | Barber |
| 2006/0110503 A1 | 5/2006 | Bates |
| 2006/0127534 A1 | 6/2006 | Elder |
| 2006/0138052 A1 | 6/2006 | Leistner |
| 2006/0163143 A1 | 7/2006 | Chirica |
| 2006/0193964 A1 | 8/2006 | Eckhoff |
| 2006/0210669 A1* | 9/2006 | Howie et al. ............ 426/45 |
| 2006/0210693 A1 | 9/2006 | Oftring |
| 2006/0216376 A1 | 9/2006 | Milici |
| 2006/0216388 A1 | 9/2006 | Christensen |
| 2007/0042080 A1 | 2/2007 | Plomp |
| 2007/0087101 A1 | 4/2007 | Gusek |
| 2007/0141225 A1 | 6/2007 | Elder |
| 2007/0141226 A1 | 6/2007 | Elder |
| 2007/0141227 A1 | 6/2007 | Boudreaux |
| 2007/0148318 A1 | 6/2007 | Rubio |
| 2007/0166439 A1 | 7/2007 | Soe |
| 2007/0178219 A1 | 8/2007 | Boudreaux |
| 2007/0184175 A1 | 8/2007 | Rubio |
| 2007/0196556 A1 | 8/2007 | Van Der Meer |
| 2007/0281062 A1 | 12/2007 | Bourg |
| 2007/0292589 A1 | 12/2007 | Elder |
| 2008/0003340 A1 | 1/2008 | Karwowski |
| 2008/0008780 A1 | 1/2008 | Streekstra |
| 2008/0101657 A1 | 5/2008 | Durkin |
| 2008/0138480 A1 | 6/2008 | Bows |
| 2008/0144880 A1 | 6/2008 | DeLuca |
| 2008/0166450 A1 | 7/2008 | Corrigan |
| 2008/0166452 A1 | 7/2008 | Corrigan |
| 2008/0253648 A1 | 10/2008 | Mulder |
| 2008/0268111 A1* | 10/2008 | Grune et al. ............ 426/231 |
| 2008/0279994 A1 | 11/2008 | Cantley |
| 2008/0299273 A1 | 12/2008 | Bhaskar |
| 2009/0047725 A1 | 2/2009 | Elder |
| 2009/0074915 A1 | 3/2009 | Hendriksen |
| 2009/0098265 A1 | 4/2009 | Kock |
| 2009/0191310 A1* | 7/2009 | Zyzak et al. ............ 426/52 |
| 2010/0040729 A1 | 2/2010 | Sahagian |
| 2010/0040750 A1 | 2/2010 | Assaad |
| 2010/0051419 A1 | 3/2010 | Desai |
| 2010/0062123 A1 | 3/2010 | Anderson |
| 2010/0143540 A1 | 6/2010 | Bhaskar |
| 2010/0255167 A1 | 10/2010 | Bourg |
| 2011/0050880 A1* | 3/2011 | Bourg et al. ............ 348/89 |

FOREIGN PATENT DOCUMENTS

| | | |
|---|---|---|
| DE | 2743230 A1 | 4/1979 |
| EP | 113940 A1 | 7/1984 |
| EP | 1419702 A1 | 5/2004 |
| EP | 1419703 A1 | 5/2004 |
| ES | 2019044 | 2/1990 |
| FR | 874453 | 8/1942 |
| GB | 156905 | 1/1921 |
| GB | 1132296 | 10/1968 |
| GB | 1519049 | 7/1978 |
| GB | 335214 | 9/1980 |
| JP | 68006927 | 9/1965 |
| JP | 70009815 | 10/1966 |
| JP | 57100179 | 12/1980 |
| JP | 62048351 A | 3/1987 |
| JP | 4104753 | 4/1992 |
| JP | 6030782 A | 2/1994 |
| JP | 06169713 | 6/1994 |
| JP | 05123126 | 5/1998 |
| JP | 10136883 | 5/1998 |
| JP | 11056280 | 3/1999 |
| JP | 11178536 | 7/1999 |
| JP | 2004180563 | 7/2004 |
| JP | 2004-313183 | 11/2004 |
| JP | 2004313183 | 11/2004 |
| JP | 2005278448 | 10/2005 |
| KR | 910006619 B1 | 8/1991 |
| RU | 2048512 | 11/1995 |
| RU | 2078797 | 5/1997 |
| RU | 2140927 | 11/1999 |
| RU | 2216574 | 11/2003 |
| SU | 1822863 | 6/1993 |
| WO | 9601572 | 1/1996 |
| WO | 0004784 | 2/2000 |
| WO | 0191581 | 12/2001 |
| WO | 2004004484 | 1/2004 |
| WO | 2004026043 | 4/2004 |
| WO | 2004028276 | 4/2004 |
| WO | 2004028277 | 4/2004 |
| WO | 2004028278 | 4/2004 |
| WO | 2004032647 | 4/2004 |
| WO | 2004032648 | 4/2004 |
| WO | 2004039174 | 5/2004 |
| WO | 2004040999 | 5/2004 |
| WO | 2004047559 | 6/2004 |
| WO | 2004060078 | 7/2004 |
| WO | 2004080205 | 9/2004 |
| WO | 2006128843 | 12/2006 |
| WO | 2007106996 | 9/2007 |
| WO | 2008061982 | 5/2008 |

OTHER PUBLICATIONS

Health Canada Food & Nutrition "Major pathway of formation of acrylamide in foods and possible approaches to mitigation" Mar. 11, 2005 (2 pages).

Health Canada OCAPI Involving You publication, "Acrylamide and Food," vol. 2, No. 1, Autumn 2002, 2 pages.

Heldman, Dennis R., et al. "Principles of Food Processing" book, 1997, p. 193.

Hughes B.P. "The amino acid composition of potato protein and of cooked potato" British J. of Nutrition, vol. 12, Issue 02, May 1958, pp. 188-195.

Igoe, Robert, Dictionary of Food Ingredients, 4th ed., (Aspen Publishers 2001), pp. 24, 35, 43, 109, and 167.

Institute of Food Science & Technology (UK) "Acrylamide Information and News" found at http://www.ifst.org/acrylmd.htm Sep. 6, 2002, 5 pages.

Ishihara, Katsuyuki, et al. "Examination of Conditions inhibiting the Formation of Acrylamide in the Model System of Fried Potato" Biosci. Biotechnol. Biochem., 70(7), 2006, pp. 1616-1621.

Jacobs, Morris B., Ph.D. "The Chemistry and Technology of Food and Food Products" textbook, 1951, pp. 221-226.

Jespersen, Neil "Chemistry" from Barron's College Review Series on Science, 1997, p. 210.

Jung, M.Y. et al. "A Novel Technique for Limitation of Acrylamide Formation in Fried and Baked Corn Chips and in French Fries", J. Food Science vol. 68, No. 4, 2003, pp. 1287-1290.

Kim, Kyu-Won, et al. "Asparaginase II of *Saccharomyces cerevisiae*" J. Biological Chem. 263 (24), Aug. 25, 1988, pp. 11948-11953.

Kim, Cheong Tae, et al. "Reducing Acrylamide in Fried Snack Products by Adding Amino Acids" J. Food Science vol. 70, Nr. 5, 2005, pp. C354-C358.

Kirk, Raymond E., et al. "Enciclopedia de Tecnologia Quimica" 1962, pp. 986-998.

Kita, Agnieszka, et al. "Effective Ways of Decreasing Acrylamide Content in Potato Crisps During Processing" J. Agric. Food Chem., Oct. 15, 2004, vol. 52, pp. 7011-7016.

Kretovich, V.L. "Plant Biochemistry" book, 1986, pp. 8-11 (English translation).

Lawrence, James E., "Acrylamide in Food" memorandum, Health Canada Food Program publication, Sep. 23, 2002, 1 page.

Low, Mei Yin, et al. "Effect of Citric Acid and Glycine Addition on Acrylamide and Flavor in a Potato Model System" J. Agric. Food Chem. 2006, 54, pp. 5976-5983.

Martin, Fiona L., et al. "Formation of Strecker Aldehydes and Pyrazines in a Fried Potato Model System" J. Agric. Food Chem. 2001, 49, pp. 3885-3892.

May, N.J., et al. "Acrylamide formation in deep-fried potato products and removal of acrylamide precursors" Food Australia 58 (10) Oct. 2006, pp. 488-493.

Mizukami, Yuzo, et al. "Analysis of Acrylamide in Green Tea by Gas Chromatography—Mass Spectrometry" J. Agric. Food Chem. 2006, 54, pp. 7370-7377.

Mottram, Don—The University of Reading, "Acrylamide in Cooked Foods—the Latest 'Food Scare'" 2002 (44 pages).

Mottram, Donald S. "Acrylamide is formed in the Maillard reaction" Nature Magazine, Oct. 3, 2002, found at www.nature.com/nature (1 page).

Murray, Lindsay, "Acrylamide" Center for Clinical Toxicology, Vanderbilt Univ. Med. Ctr., Jul. 1996 found at http://www.inchem.org/documents/pims/chemical/pim652.htm, Jun. 1998 (8 pages).

Mustafa, Arwa, et al. "Factors Influencing Acrylamide Content and Color in Rye Crisp Bread" J. Agric. Food Chem. 2005, 53, pp. 5985-5989.

Neergaard, Lauran "Scientists: Chemical Reaction May Create Carcinogen" Health Zone found at http://www.cjonline.com/stories/093002/hea_carcinogen.shtml, Sep. 30, 2002 (3 pages).

Nielsen, Per Munk "Enzyme Technology for Production of Protein-Based Flavours" Novo Nordisk A/S 1995 (6 pages).

Ou, Shiyi, et al. "Reduction of Acrylamide Formation by Selected Agents in Fried Potato Crisps on Industrial Scale" ScienceDirect, Innovative Food Science and Emerging Technologies 9 (2008) pp. 116-121.

Pedreschi, Franco, et al. "Acrylamide reduction under different pre-treatments in French fries" ScienceDirect Journal of Food Engineering 79 (2007) pp. 1287-1294.

Pedreschi, Franco, et al. "Color development and acrylamide content of pre-dried potato chips" ScienceDirect Journal of Food Engineering 79 (2007) pp. 786-793.

Pedreschi, Franco, et al. "Color kinetics and acrylamide formation in NaCI soaked potato chips" ScienceDirect Journal of Food Engineering 79 (2007) pp. 989-997.

Pedreschi, Franco, et al. "Reduction of Acrylamide Formation in Potato Slices During Frying" Lebensm.-Wiss u.-Technol. 37 (2004) pp. 679-685.

Procter & Gamble Press Release Sep. 27, 2002 "Procter & Gamble Makes Significant Advances on Understanding Acrylamide Formation" found at http://biz.yahoo.com/prnews/020927/clf005_1.html (2 pages).

Raloff, Janet, "Hot Spuds: Golden Path to Acrylamide in Food" Science News Online, Oct. 5, 2002, vol. 162 found at http://www.sciencenews.org/20021005/fob5.asp (3 pages).

Rossell, J.B. (ed.) "Frying—Improving Quality" CRC Press, 2001, pp. 198-214 and 306-308.

Rydberg, Per, et al. "Investigations of Factors That Influence the Acrylamide Content of Heated Foodstuffs" J. Agric. Food Chem. 2003, vol. 51, pp. 7012-7018.

Sanders, R.A., et al. "An LC/MS Acrylamide Method and Its Use in Investigating the Role of Asparagine," printout of presentation slides (24 pages).

Segtnan, Vegard H., et al. "Screening of acrylamide contents in potato crisps using process variable settings and near-infrared spectroscopy" Mol. Nutr. Food Res. vol. 50, 2006, pp. 811-817.

Stadler, Richard H., et al. "Acrylamide from Maillard reaction products" Nature Magazine Oct. 3, 2002 found at www.nature.com/nature (2 pages).

Talburt & Smith (eds.), Potato Processing 4th Ed. 1987, Ch. 12 "Dehydrated Mashed Potatoes—Potato Granules," pp. 535-555.

Talburt & Smith (eds.), Potato Processing 4th Ed. 1987, "Improving the Color of Potato Chips," pp. 403-405.

Tareke, Eden, et al., "Analysis of Acrylamide, a Carcinogen Formed in Heated Foodstuffs," J. Agric. Food Chem. pp. A through I.

"Temperature and Heat—Local Materials" Mar. 2003 found at http://web.archive.org/web/20030321105136/http://www.pa.uky.edu/sciworks/xtra/local.htm (3 pages).

U.S. Dept. of Health and Human Services, Public Health Service, National Toxicology Program, "9th Report on Carcinogens Revised Jan. 2001" found at http://win2000.kreatiweb.it/sanitaweb/web/Biblioteca/carcinogens/rahc/acrylamide.pdf (5 pages).

U.S. Dept. of Health & Human Services, U.S. Food and Drug Adm., Center for Food Safety and Applied Nutrition "Exploratory Data on Acrylamide in Foods" Dec. 4, 2002 found at http://www.mindfully.org/food/acrylamide-foods-fda (9 pages).

U.S. Food and Drug Administration Public Meeting "Assessing Acrylamide in the U.S. Food Supply," Sep. 30, 2002(5 pages).

Viklund, Gunilla A., et al., "Variety and Storage Conditions Affect the Precursor Content and Amount of Acrylamide in Potato Crisps," J. Sci. Food Agric. 2008, vol. 88, pp. 305-312.

Vivanti, Vittorio, et al. "Level of Acrylamide Precursors Asparagine, Fructose, Glucose, and Sucrose in Potatoes Sold at Retail in Italy and in the United States" J. Food Science, vol. 71, Nr. 2, 2006, pp. C81-C85.

Watson, S.A. (ed.), Corn: Chemistry and Technology, American Association of Cereal Chemists, 1987, pp. 410-420.

Webb, Edwin C., "Enzyme Nomenclature 1992," Academic Press, p. 422.

Decision of Rejection, Japanese Pat. App. No. 2007-544461 dated Mar. 16, 2010, translated into English (2 pages).

"Kagaku Dai-jiten (Encyclopedia of Chemistry)," edited by Ohki Michinori, et al., 1989, pp. 317, 96, and 1661 (6 pages).

"Shokuhin Tenkabutsu Binran (List of Food Additives)," 1964, p. 249 (2 pages).

Standard Electrode Potentials, http://www.benjamin-mills.com/chemistry/ecells.htm (2 pages).

AFSSA, French Food Safety Agency, "Acrylamide: Information Point," Jul. 24, 2002 (11 pages).

Rufian-Henares, J.A., et al., "Determination of acrylamide in potato chips by a reversed-phase LC-MS method based on a stable isotope dilution assay," Food Chemistry vol. 97, No. 3, Aug. 1, 2006, pp. 555-562.

Pedreschi, Franco, et al. "Color changes and acrylamide formation in fried potato slices," Food Research International, vol. 38, No. 1, Jan. 1, 2005, pp. 1-9.

Zhang, Yu, et al., "Occurrence and analytical methods of acrylamide in heat-treated foods—Review and recent developments," Journal of Chromatography, Elsevier Science Publishers, vol. 1075, No. 1-2, May 20, 2005, pp. 1-21.

Stark, Jeffrey C., et al., "Tuber Quality" date unknown, found at http://www.cals.uidaho.edu/potato/ PotatoProductionSystems/Topics/TuberQuality.pdf 15 pages.

Weaver, M.L., et al., "Sugar-End in Russet Burbank Potatoes," American Journal of Potato Research, 1972, vol. 49, No. 10, pp. 376-382.

Dobarganes, Carmen, et al., "Interactions between fat and food during deep-frying," Eur. J. Lipid Sci. Tech. 2000, vol. 102, pp. 521-528.

Erickson, Michael D., ed., Book entitled "Deep Frying—Chemistry, Nutrition and Practical Applications," 2d edition, pp. 262, 263, 274, 275.

Farid, M.M., et al., "The analysis of heat and mass transfer during frying of food using a moving boundary solution procedure," Heat and Mass Transfer, vol. 34, 1998, pp. 69-77.

Fleck, Fiona, "Experts launch action on acrylamide in staple foods," British Medical Journal, Jul. 20, 2002, p. 120.

Jackson, Lauren, "Formation of acrylamide in food," US FDA Centre for Food Safety and Applied Nutrition, National Centre for Food Safety and Technology, Summit—Argo, IL, Dec. 4-5, 2002 presentation, 32 pages.

Lotfi, Ehsan, et al. "A new approach for automatic quality control of fried potatoes using machine learning," Islamic Azad University, Mashad Branch, Ferdowsi University of Mashad, Khorasan Research Center for Technology Development, Mar. 11, 2009, 4 pages.

Pedreschi, Franco, et al. "Acrylamide content and color development in fried potato strips," ScienceDirect Journal of Food Engineering 39 (2006) pp. 40-46.

Research Disclosure 15172, New process for the manufacture of potato-chips from different types of potatoes (not selected), Nov. 1976, 1 page.

Talburt & Smith (eds.), Potato Processing 4th Ed. 1987, "Improving the Color of Potato Chips," pp. 406-413.

Tareke, E., et al., "Acrylamide: A Cooking Carcinogen?" Chem. Res. Toxicol. 2000, vol. 13, pp. 517-522, Published on Web May 27, 2000 (6 pages).

NFRI Report, published Jul. 1, 2004, Report on the symposium named "Chemistry and Safety of Acrylamide in Food" held by the Agricultural and Food Chemistry Division of the American Chemical Society held on Mar. 28-31, 2004 in Anaheim, CA, USA, published by the National Food Research Institute (NFRI) of the National Agricultural and Food Research Organization of Japan (NARO), available at http://oasys2.confex.com/acs/227nm/techprogram/D941.HTM.

Summary Report of "2004 Acrylamide in Food Workshop: Update—Scientific Issues, Uncertainties, and Research Strategies," held on Apr. 13-15, 2004 in Chicago, IL, USA, published on Aug. 6, 2004, by the National Food Research Institute (NFRI) of the National Agricultural and Food Research Organization of Japan (NARO), available at http://222.jifsan.umd.edu/docs/acry2004.

Martinez-Bustos, F., "Effect of the components of maize on the quality of masa and tortillas during the traditional nixtamalisation process," Journal of the Science of Food and Agriculture, vol. 81, pp. 1455-1462, Aug. 13, 2001, 8 pages.

Sefa-Dedeh, S., "Effect of nixtamalization on the chemical and functional properties of maize," Food Chemistry, vol. 86, pp. 317-324, Aug. 14, 2003, 8 pages.

Weisshaar, Rudiger, et al. "Formation of Acrylamide in Heated Potato Products—Model Experiments Pointing to Asparagine as Precursor" Pub. Oct. 3, 2002, Deutsche Lebensmittel-Rundschau 98 Jahrgang, Heft (4 pages).

Williams, J.S.E., "Influence of Variety and Processing Conditions on Acrylamide Levels in Fried Potato Crisps," ScienceDirect Food Chemistry 90 (2005), pp. 875-881.

"Working Group 1: Mechanisms of Formation of Acrylamide in Food" Summary Report(7 pages).

Wulfsberg, Gary, Inorganic Chemistry book, University Science Books, 2000,p. 289.

Yarnell, Amanda, "Acrylamide Mystery Solved," Chemical & Engineering News, Oct. 4, 2002 found at http://pubs.acs.org/cen/today/oct4.html (3 pages).

Yaylayan, Varoujan A., et al., "Why Asparagine Needs Carbohydrates to Generate Acrylamide," J. Agric. Food Chem. 2003, vol. 51, pp. 1753-1757.

Zhang, Yu, et al., "Study on Formation of Acrylamide in Asparagine-Sugar Microwave Heating Systems Using UPLC-MS/MS Analytical Method," ScienceDirect, Food Chemistry 108 (2008), pp. 542-550.

Zyzak David V. et al., "Acrylamide Formation Mechanism in Heated Foods," J. Agric. Food Chem. 2003, vol. 51, pp. 4782-4787.

Zyzak, David, et al. v. Elder, Vincent Allen, et al., Board of Patent Appeals and Interferences, Judgment-Arbitration-Bd.R. 126(f),Apr. 14, 2008, 2 pages.

Abdel-Kader, Zakia M., "Effect of blanching on the diffusion of glucose from potatoes" (Abstract), Wiley InterScience Journals: Nahrung / Food vol. 36, Iss. 1, 1992, 1 page.

Abstracts of literature search, "Pathway from Asparagine to Acrylamide," 17 pages.

Alternative Medicine Review "Glutathione, Reduced (GSH)" vol. 6, No. 6, 2001, pp. 601-607.

Amrein, Thomas, "Influence of Thermal Processing Conditions on Acrylamide Generation and Browning in a Potato Model System," J. Agric. Food Chem. 2006, 54, pp. 5910-5916.

Ashoor, S.H. & Zent, J.B., "Maillard Browning of Common Amino Acids and Sugars," (Abstract), Wiley InterScience Journals: J. Food Science, vol. 49, Issue 4, Jul. 1984, 2 pages.

Associated Press Washington—"Habrian descubierto el origen de sustancia cancerigena en las papas fritas," Sep. 30, 2002, 2 pages.

Becalski, Adam, et al., "Acrylamide in Foods: Occurrence, Sources, and Modeling," J. Agric. Food Chemistry, 2003, vol. 51, pp. 802-808.

Becalski, Adam, et al., "Acrylamide in French Fries: Influence of Free Amino Acids and Sugars," (Abstract), J. Agric. Food Chem. 52 (12), May 22, 2004, 1 page.

Bosset, Dr. Jacques Olivier, et al. "Mitteilungen aus Lebensmitteluntersuchung und Hygiene" Jun. 2002, vol. 93, Offizielles Organ der Schweizerischen Gesellschaft fur Lebensmittel-und Umweltchemie und der Schweizerischen Gesellschaft fur Lebensmittelhygien(79 pages).

Brathen, Erland, et al., "Addition of Glycine Reduces the Content of Acrylamide in Cereal and Potato Products," J. Agric. Food Chem. 2005, vol. 53, pp. 3259-3264.

CBC News CBC.CA "Food sector told to cut down on toxins in chips, fries" Sep. 19, 2002, 2 pages.

CBC News CBC.CA "Scientists find route for toxin to form in fried, baked foods," Sep. 30, 2002, 3 pages.

CBC News CBC.CA "Some acrylamide with your fries?" Jan. 14, 2003, 6 pages.

Center for Science in the Public Interest article "New Tests Confirm Acrylamide in American Foods," found at http://www.cspinet.org/new/200206251.html, Jun. 25, 2002, 2 pages.

Centre for Molecular and Biomolecular Informatics article "An Amino Acid Bedtime Story" found at http://www.cmbi.kun.nl.gvteach/HAN/alg/infopages/bedtime.html, material from Friedli Enterprises, Gert Vriend, Apr. 18, 2000, 4 pages.

chemhelper.com Home Page for Frostburg State University—Organic Chemistry Help, article "Nucleophilic Addition to Carbonyl Groups" found at http://www.chemhelper.com/nucadd.html, 2000 (3 pages).

Claeys, Wendie L., et al. "Quantifying the formation of carcinogens during food processing: acrylamide," Trends in Food Science & Technology 16 (2005), pp. 181-193.

Database WPI Week 199329 Derwent Publications Ltd., London, GB; AN 1993-234163 XP002473734 & SU 1 750 586 A1 (Interbios Res Assoc) Jul. 30, 1992, 1 page.

Database WPI Week 199805 Thomson Scientific, London, GB; AN 1998-042903 XP002503379, Dec. 4, 1996, 1 page.

de Barber, C. Benedito de, et al. "Reversed-Phase High-Performance Liquid Chromatography Analysis of Changes in Free Amino Acids During Wheat Bread Dough Fermentation" Cereal Chemistry, Feb. 26, 1989, vol. 66, No. 4, pp. 283-288.

de Meulenaer, Bruno, et al., "Comparison of Potato Varieties Between Seasons and Their Potential for Acrylamide Formation," J. Science Food Agric., vol. 88, 2008, pp. 313-318.

de Vleeschouwer, Kristel, et al., "Impact of pH on the Kinetics of Acrylamide Formation/Elimination Reactions in Model Systems," J. Agric. Food Chem. vol. 54, 2006, pp. 7847-7855.

de Wilde, Tineke, et al., "Influence of Fertilization on Acrylamide Formation during Frying of Potatoes Harvested in 2003," J. Agric. Food Chem., 2006, vol. 54, pp. 404-408.

Dunlop, Patricia C., et al. "Nitrogen Catabolite Repression of Asparaginase II in *Saccharomyces cerevisiae*" J. Bacteriology, Jul. 1980, vol. 143, No. 1, pp. 422-426.

El Pais.com, "Hallada la reaccion quimica que produce la acrilamida en las frituras," Jul. 15, 2009, 1 page.

European Commission—Health and Consumer Protection Directorate-General, "Opinion of the Scientific Committee on Food on new findings regarding the presence of acrylamide in food," Jul. 3, 2002, 16 pages.

European Food Safety Authority, Report of "Workshop on Acrylamide Formation in Food," Nov. 17, 2003, Brussels, 22 pages.

"FAO/WHO Joint Consultation on the Health Implications of Acrylamide in Food" Summary Report, Geneva, Switzerland, Jun. 25-27, 2002, 12 pages.

Food Safety Consultations "Health Implications of Acrylamide in Food" Report of a Joint FAO/WHO Consultation, Geneva, Switzerland, Jun. 25-27, 2002, 38 pages.

Joint FAO/WHO Expert Commission on Food Additives, 64th Meeting, Rome, Feb. 8-17, 2005, 47 pages.

Fan, Xuetong, et al. "Effectiveness of Ionizing Radiation in Reducing Furan and Acrylamide Levels in Foods" J. Agric. Food Chem. 2006, 54, pp. 8266-8270.

Fiselier, K, et al., "Brown potato Croquettes Low in Acrylamide by Coating with Egg/Breadcrumbs," Eur. Food Res. Technol. (2004) 219:111-115.

Fiselier, Katell, et al., "Higher Acrylamide Contents in French Fries Prepared from "Fresh" Prefabricates," Eur. Food Res. Technol. (2005) 221:376-381.

Food Standards Agency, "Study of Acrylamide in Food," May 17, 2002, 7 pages.

Francis, Frederick J., "Encyclopedia of Food Science and Technology," 2nd ed., 2000, pp. 2160-2161.

Freshfields Bruckhaus Deringer "Acrylamide in food—The approach of regulators across Europe" Feb. 2003 (20 pages).

Friedman, Mendel, et al., "Browning prevention in fresh and dehydrated potatoes by SH-containing amino acids," Food Additives and Contaminants, 1992, vol. 9, No. 5, pp. 499-503.

Friedman, Mendel, "Chemistry, BioChemistry, and Safety of Acrylamide. A Review," J. Agric. Food Chem., Jul. 3, 2003, vol. 51 (16), pp. 4504-4526.

Friedman, Mendel, et al., "Inhibition of Browning by Sulfur Amino Acids. 1. Heated Amino Acid-Glucose Systems," J. Agric. Food Chem., 1990, 38, pp. 1641-1647.

Friedman, Mendel "The Impact of the Maillard Reaction on the Nutritional Value of Food Proteins" Ch. 6 from The Maillard Reaction: Consequences for the Chemical and Life Sciences, Ikan, Raphael (ed.), 1996, 24 pages.

Garayo, Jagoba, et al. "Vacuum frying of potato chips" J. Food Engineering 55 (2002), pp. 181-191.

Gertz, Christian, et al. "Analysis of acrylamide and mechanisms of its formation in deep-fried products" Eur. J. Lipid Sci. Technol. 104 (2002), pp. 762-771.

Gokmen, Vural, et al., "Acrylamide formation is prevented by divalent cations during the Maillard reaction," Food Chemistry (2006) doi: 10.1016/j.foodchem.2006.08.011, 8 pages.

Granda, Claudia, et al., "Effect of Raw Potato Composition on Acrylamide Formation in Potato Chips," J. Food Science vol. 70, Nr. 9, 2005, Nov. 16, 2005, pp. E519-E525.

Granda, Claudia, et al. "Kinetics of Acrylamide Formation During Traditional and Vacuum Frying of Potato Chips" J. Food Process Engineering 28 (2005), pp. 478-493.

Granda, C., et al. "Reduction of Acrylamide Formation in Potato Chips by Low-temperature Vacuum Frying", J. Food Science, vol. 69, Nr. 8, 2004, Oct. 7, 2004, pp. E405-E411.

Grivas, Prof. Spiros, et al. "Acrylamide in Food—Mechanisms of Formation and Influencing Factors During Heating of Foods", Report from Swedish Scientific Expert Committee, Apr. 24, 2002 (22 pages).

Harmony House Foods, Inc., http://web.archive.org/web/20050425210612/www.harmonyhousefoods.com/slicedpotato.html, Apr. 25, 2005, 2 pages.

Harrison, Karl "Amino Acids and Proteins" found at http://www.chem.ox.ac.uk/mom/amino_acids/introduction.html, 1996 (2 pages).

Harrison, Karl "Molecules of the Month" found at http://www.chem.ox.ac.uk/mom/, 1996 (1 page).

* cited by examiner

METHOD FOR REAL TIME MEASUREMENT OF ACRYLAMIDE IN A FOOD PRODUCT

CROSS-REFERENCE TO RELATED APPLICATIONS

This application claims the benefit of U.S. Provisional Application No. 61/092,513 filed Aug. 28, 2008.

BACKGROUND OF THE INVENTION

1. Technical Field

This invention relates to the use of wavelength emission data for the real time quantitative analysis of acrylamide levels in food.

2. Description of Related Art

In recent times, a wide variety of foods have tested positive for the presence of acrylamide monomer. Acrylamide has especially been found primarily in carbohydrate food products that have been heated or processed at high temperatures. Examples of foods that have tested positive for acrylamide include coffee, cereals, cookies, potato chips, crackers, pretzels, french-fried potatoes, breads and rolls, and fried breaded meats. In general, relatively low contents of acrylamide have been found in heated protein-rich foods, while relatively high contents of acrylamide have been found in carbohydrate-rich foods, compared to non-detectable levels in unheated and boiled foods.

Acrylamide has not been determined to be detrimental to humans, but its presence in food products may be undesirable. As noted previously, relatively higher concentrations of acrylamide are found in food products that have been heated or thermally processed. The reduction of acrylamide in such food products could be accomplished by reducing or eliminating the precursor compounds that form acrylamide, inhibiting the formation of acrylamide during the processing of the food, or removing acrylamide from the product prior to consumption.

The measurement of acrylamide in food products is a time consuming procedure. U.S. Patent Application Publication No. 2006/0029992 discloses two ways to detect and quantify the acrylamide content in food products. The first way is liquid chromatography in tandem with mass spectrometry (LC-MS/MS) and the second way is gas chromatography-mass spectrometry (GC-MS). These two tests require an extensive lab environment and a lab professional to conduct the testing. The tests are therefore time intensive and fail to provide a quick way to test for acrylamide in food products. Consequently, a need exists for a real-time way to measure acrylamide levels in food products.

One article (Segtnan, et al, "Screening of acrylamide contents in potato crisps using process variable settings and near-infrared spectroscopy," *Mol. Nutr. Food. Res.* 2006 50, 811-817), the entirety of which is hereby incorporated by reference, discloses measuring NIR spectra with the focus of the spectral analysis occurring on bands originating from water, carbohydrates, and fat rather than the amide bonds. The highest R-value disclosed in the article is a value of 0.952, meaning the highest R-squared value, which is an indicator of correlation between predicted and actual values is 0.906. A need exists for a more accurate predictor of acrylamide concentration in a food product.

Further, while it would be desirable to measure on a real time basis the level of acrylamide in a food product being produced on a commercial food product manufacturing line, it would also be desirable to use real time acrylamide measurements to reduce the level of acrylamide in a food product on a real time basis. Consequently, such heightened accuracy of a real-time acrylamide measurement is especially important if the real-time measured value of acrylamide is used to adjust process variables to manually or automatically lower the acrylamide level in a food product being manufactured on a food manufacturing line.

One prior art method for reducing acrylamide in food products, as illustrated by U.S. Pat. No. 7,393,550, assigned to the same assignee as the present invention, occurs by heating the food product at lower temperatures when the food has achieved lower moisture contents. Thus, a potato slice can be par-fried to a moisture content of 4% and finish dried in an oven at a temperature of less than 120° C. until a moisture content of less than 2% is achieved. However, it is very difficult to monitor and/or control many of the variables affecting the formation of acrylamide in individual food pieces, even when such pieces are manufactured on the same food manufacturing or production line. For example, individual potato chips made by a par-fry process can still have different levels of acrylamide because some potato chips may stay in the fryer longer than other chips, or some raw potatoes may have higher levels of reducing sugars, or some raw potatoes may have other defects that cause high levels of acrylamide. Consequently, a need exists for a way to reduce the variability of acrylamide levels in food products in a food manufacturing line. A need also exists to use a real-time acrylamide monitoring and measurement system to control the food manufacturing process to minimize the amount of acrylamide level in a final food product. A need also exists for a method and system for making food products having more consistent levels of acrylamide. A need also exists to be able to remove, on a real-time basis, foods formed in a food manufacturing process that have acrylamide levels above a certain threshold.

SUMMARY OF THE INVENTION

One aspect of the present invention is directed towards a method for the real time measurement of acrylamide levels in a food product comprising the steps of collecting wavelength emission data for each of a plurality of food products, testing each of said plurality of food products in an analytical laboratory for an off-line acrylamide level or for an off-line acrylamide pre-cursor level and correlating said analytical laboratory data with said wavelength emission data. In one aspect, the invention further comprises using the real time measurement of acrylamide level and adjusting a process variable in the food manufacturing line to lower the level of acrylamide in the food product. In one aspect, the invention further comprises removal of food products having an acrylamide level above a certain threshold prior to a packaging step.

Other aspects, embodiments and features of the invention will become apparent from the following detailed description of the invention when considered in conjunction with the accompanying drawings. The accompanying figures are schematic and are not intended to be drawn to scale. In the figures, each identical, or substantially similar component that is illustrated in various figures is represented by a single numeral or notation. For purposes of clarity, not every component is labeled in every figure. Nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

BRIEF DESCRIPTION OF THE DRAWINGS

The novel features believed characteristic of the invention are set forth in the appended claims. The invention itself, however, as well as a preferred mode of use, further objectives and advantages thereof, will be best understood by reference to the following detailed description of illustrative embodiments when read in conjunction with the accompanying drawings, wherein:

DETAILED DESCRIPTION

Figure 1:
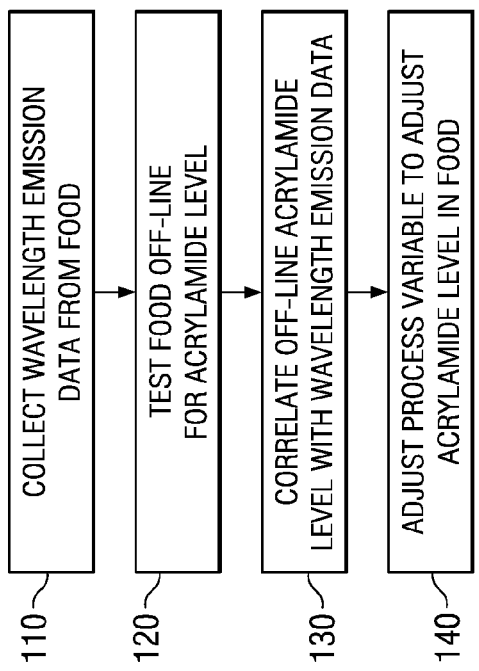
FIG. 1 depicts a general flow chart of a method for monitoring the acrylamide level in a food product in accordance with one embodiment of the present invention.

The present invention, in one embodiment, comprises a method for real-time monitoring of the acrylamide level in a food product. FIG. 1 depicts a general flow chart of a method for monitoring the acrylamide level in a food product in accordance with one embodiment of the present invention. Referring to FIG. 1, food products are illuminated with a broad spectrum or near infrared wavelength energy and the intensity that is reflected back at various wavelengths, defined herein as wavelength emission data, is measured for evaluation and analysis. As used herein, the terms "wavelength emission data" and "wavelength reflectance data" are synonymous, and refer to the intensity reflected back at various wavelengths.

The wavelength ("λ") of electromagnetic radiation is related to the frequency by the formula $$c = v\lambda$$

Where
$c = 3 \times 10^8$ m/s (velocity of light)
$\lambda$ = wavelength (m)
$v$ = frequency ($s^{-1}$ or Hz)

Figure 5:
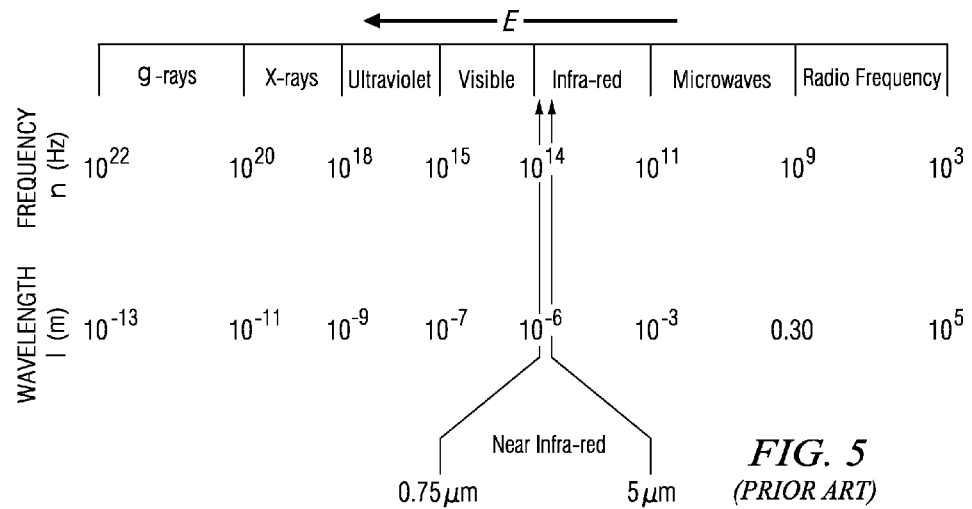
FIG. 5 is a prior art depiction of the real time wavelengths and energies in the electromagnetic spectrum that are used in spectroscopy.

Wavelength emission data can be collected from any number of ranges, including but not limited to the near infrared range ("NIR") (from about 750 nanometers to 5000 nanometers), the mid-infrared range (5000 nanometers to 25000 nanometers), the long infrared range (25000 nanometers to 350 micrometers) and/or from the visible color range (380 nanometers to 750 nanometers), as depicted in FIG. 5, which is a prior art depiction of the relative wavelengths and energies in the electromagnetic spectrum that are used in spectroscopy. Each of these ranges can have information helpful to determine the level of acrylamide pre-cursors and/or the level of acrylamide in a food product. As used herein, an acrylamide pre-cursor includes 1) any reactant that forms acrylamide, 2) any indicator of acrylamide formation, or 3) a compound having a degradation product that is a reactant that forms acrylamide.

By way of example, it is known that acrylamide is formed when asparagine is reacted with reducing sugars and heat in excess of about 120° C. Consequently, for purposes of this invention, asparagine and reducing sugars (e.g., fructose, maltose, lactose, dextrose, glucose) are acrylamide pre-cursors because they are reactants that form acrylamide. Further, because heat is necessary for the reaction to take place, heat is an acrylamide pre-cursor for purposes of this invention. In one embodiment, heat in excess of about 120° C. is an acrylamide pre-cursor in accordance with one embodiment of the present invention. In one embodiment a food temperature of between about 120° C. and about 225° C. can be an indicator of acrylamide formation. Acrylamide pre-cursor reactants such as reducing sugars can be quantitatively analyzed using NIR spectral responses.

Indicators of acrylamide formation (e.g., acrylamide pre-cursors) can include any of the free amino acids that participate in the Maillard browning reactions along with reducing sugars. Further, because sucrose consists of two reducing sugars (glucose and fructose) and water, the reducing sugars are potential degradation products of sucrose. When sucrose is exposed to heat, it decomposes into reducing sugars and these reducing sugars are acrylamide pre-cursors. Consequently, for purposes of this invention, sucrose is an acrylamide pre-cursor because sugar is a compound having degradation products (e.g., glucose and/or fructose) that are reactants that form acrylamide. It should be noted that the sucrose concentration is in the range of about 10 times the reducing sugar concentration in chipping potatoes.

Heat gradients that can indicate heating or cooling rates can also be indicators of acrylamide formation. Consequently, heat gradients are acrylamide pre-cursors in accordance with the present invention.

Referring back to FIG. 1, the food from which wavelength emission data was collected 110 is tested off-line in an analytical laboratory 120 for levels of acrylamide and/or acrylamide pre-cursors. The analytical laboratory tests 120 used can be selected from laboratory tests (e.g., GC-MS, LC-HRMS) known to be reliable in the art.

The wavelength emission data can then be correlated 130 with the off-line acrylamide level 120. For example, if the wavelength emission data collected is from the near infrared range for samples 1-10, the wavelength emission data can be loaded into a commercial software program, such as Simca P+ available from Umetrics Inc. of Kennelon, N.J. The near infrared range can be used to detect wavelength emission data corresponding to compounds associated with the Maillard Browning Reaction, as revealed by the wavelength regions that identify aldehyde and ketone compounds, and to detect wavelength emission data responsive to the precursors such as free amino acids, sugars, and chlorides. The corresponding analytical data from GC-MS tests can also be input into the software program and the correlation between the wavelength emission data and the off-line analytical laboratory test data can be made using multivariate analysis to identify regions of wavelength that correspond to acrylamide levels. Specifically, correlation can be made by preprocessing the wavelength emission data through a derivative algorithm (e.g., such as one provided by Simca P+ software), then subjecting the resultant spectra through a Projection of Latent Structures "PLS" algorithm (also available in the Simca P+ software). Thus, the present invention provides a way to use actual empirical data collected from food samples to predict acrylamide levels in food samples on a real time, non-destructive basis. Reliable, real-time acrylamide measurements can then be used to adjust process variables to adjust the levels of acrylamide in the finished food product 140, as will be discussed in more detail below.

Figure 2:
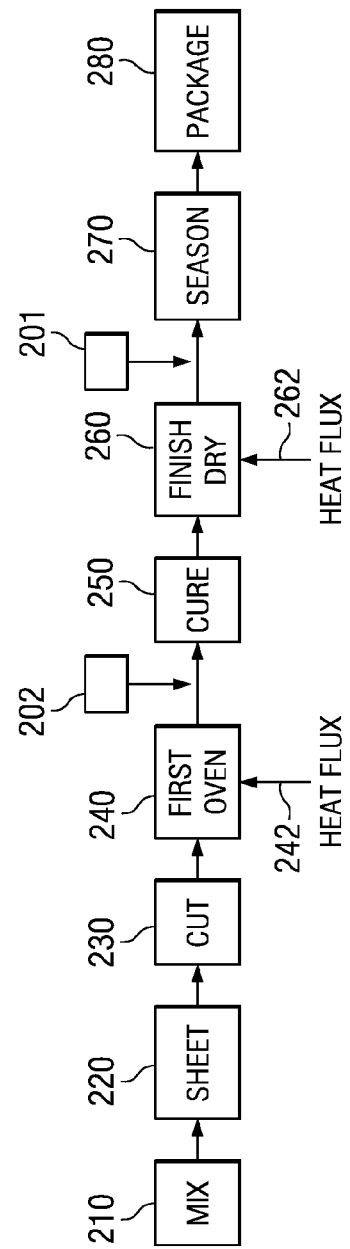
FIG. 2 depicts a general flow chart of a method for monitoring the acrylamide level in a food product in accordance with one embodiment of the present invention.

FIG. 2 depicts a general flow chart of a method for monitoring the acrylamide level in a fabricated snack in accordance with one embodiment of the present invention. Such Figure is provided merely for purposes of illustration and not limitation. Those having ordinary skill in the art, armed with this disclosure will be able to apply to present invention to many food manufacturing process lines. The term "fabricated snack" means a snack food that uses as its starting ingredient something other than the original and unaltered starchy starting material. For example, fabricated snacks include fabricated potato chips that use a dehydrated potato product as a starting material and corn chips that use masa flour as its starting material. It is noted here that the dehydrated potato product can be potato flour, potato flakes, potato granules, or other forms in which dehydrated potatoes exist. When any of these terms are used in this application, it is understood that all of these variations are included. By way of example only, and without limitation, examples of "fabricated foods" to which an acrylamide-reducing agent can be added include tortilla chips, corn chips, potato chips made from potato flakes and/or fresh potato mash, multigrain chips, corn puffs, wheat puffs, rice puffs, crackers, breads (such as rye, wheat, oat, potato, white, whole grain, and mixed flours), soft and hard pretzels, pastries, cookies, toast, corn tortillas, flour tortillas, pita bread, croissants, pie crusts, muffins, brownies, cakes, bagels, doughnuts, cereals, extruded snacks, granola products, flours, corn meal, masa, potato flakes, polenta, batter mixes and dough products, refrigerated and frozen doughs, reconstituted foods, processed and frozen foods, breading on meats and vegetables, hash browns, mashed potatoes, crepes, pancakes, waffles, pizza crust, peanut butter, foods containing chopped and processed nuts, jellies, fillings, mashed fruits, mashed vegetables, alcoholic beverages such as beers and ales, cocoa, cocoa powder, chocolate, hot chocolate, cheese, animal foods such as dog and cat kibble, and any other human or animal food products that are subject to sheeting or extruding or that are made from a dough or mixture of ingredients. The use of the term "fabricated foods" herein includes fabricated snacks as previously defined. The use of the term "food products" herein includes all fabricated snacks and fabricated foods as previously defined.

As referred to herein, the thermally-processed foods include, by way of example and without limitation, all of the foods previously listed as examples of fabricated snacks and fabricated foods, as well as french fries, yam fries, other tuber or root materials, cooked vegetables including cooked asparagus, onions, and tomatoes, coffee beans, cocoa beans, coffee, cooked meats, dehydrated fruits and vegetables, dried foods such as soup and dip mixes, heat-processed animal feed, tobacco, tea, roasted or cooked nuts, soybeans, molasses, sauces such as barbecue sauce, plantain chips, apple chips, fried bananas, and other cooked fruits that have been thermally processed at food temperatures exceeding about 120° C.

The process depicted in FIG. 2 can be used, for example, to make baked potato chips, pretzels, or pita chips. Raw ingredients, such as potato flakes, water, and starches are mixed together in a mixer 210 to make a dough having a moisture content of between about 30% and about 40%. The dough can be sheeted in a sheeter 220 and cut by a cutter 230 into pre-forms. The pre-forms can be routed in a monolayer fashion to a first oven 240. In one embodiment, the first oven is a gas-fired impingement oven. Here the pre-forms can be exposed to oven temperatures of between about 300° F. and about 600° F. for between about 90 seconds and about 35 minutes. The temperature of the food product surface exiting the first oven 240 operating at such temperature range can be from between about 220° F. and about 365° F. and the moisture content of the pre-forms exiting the first oven 240 is typically about 9% to about 12% by weight. The pre-forms can then be sent through a curing stage 250 where pre-forms are exposed to ambient air for about 15 seconds to about 3 minutes to equilibrate moisture throughout the pre-form. The pre-forms can then be sent to a multi-zone finish drying oven operating at oven temperatures of between about 230° F. to 310° F. and having a food product surface temperature of between about 220° F. and about 290° F. to lower the moisture content below about 2% by weight, and in one embodiment between about 0.5% to about 2% by weight. The product can then be seasoned 270 and packaged 280. Unlike the first oven 240 where the pre-forms are in a monolayer arrangement, the pre-forms in the second oven can be bedded to about two to eight inches.

Because acrylamide can be formed in the food product when the food product is in the first oven 240 and in the second oven 260, acrylamide can be monitored by measuring the acrylamide levels of the pre-forms as the pre-forms exit either or both ovens. In one embodiment, a near infrared camera 201 is used above the bed of product exiting the second oven 260 to gather wavelength emission data in the near infrared range from a first sample of food product. This same first sample of food product is then tested by GC-MS in an analytical laboratory for levels of acrylamide and/or acrylamide pre-cursors such as asparagine and/or reducing sugars using one or more of the analytical laboratory test methods known in the art. This process can be repeated with a second sample of food product and so on with as many samples as desired to enhance accuracy and precision of the resultant model. The wavelength emission data from the near infrared detector can then be correlated with the analytical laboratory data from the GC-MS with commercial software. Consequently, the present invention provides a method and system for providing real-time measurement of acrylamide in food products once the wavelength emission data has been correlated with the analytical data. In one embodiment, the real-time measurement occurs at the outlet of a dehydration unit such as an oven or a fryer.

In one embodiment, Fourier Transform Infra-red Spectroscopy (FTIR) spectrograms of food products having a desired acrylamide level are analyzed with commercial software programs using such techniques as Principal Component Analysis (PCA) and for Projection of Latent Structures (PLS) to characterize a "fingerprint" of a low or reduced acrylamide food product. By way of example, a food having a desired, reduced level of acrylamide can be a fried potato slice having an acrylamide level of less than about 100 ppb. Once the FTIR spectrogram for such fried potato slice is established, very small deviations from the "fingerprint" can be detected. For example, it has been discovered that acrylamide and a group of pyrazine compounds are highly correlated based on results using analytical laboratory tests such as GC-MS. The pyrazine compounds are related to Maillard browning reactions that result from chemical reactions between amino acids and reducing sugars at elevated temperatures. Consequently, changes in the infrared spectral response of products produced in high acrylamide forming environments can be detectably different than food products formed in low acrylamide forming environments. Consequently, changes in the infrared spectra of the finished product can be an additional indicator of the acrylamide level in a food product.

Reliable, real-time acrylamide measurements, whether provided by NIR or FTIR, can then be used to adjust process variables to adjust the levels of acrylamide in a finished food product. For example, the time and temperature of exposure of a food product in the second oven 260 can be optimized so as to minimize the level of acrylamide in the finished food product. For example, if the level of acrylamide exiting the second oven 260 is above a desired threshold, then the heat flux 262 of the second oven 260 can be adjusted downward and the residence time in the oven can be adjusted upward by slowing the conveyor speed so that the food product still exits the oven with at the desired moisture level.

As discussed above, often times there are differences in acrylamide levels in food product made on the same manufacturing line. For example, a gas-fired impingement oven can be used as a first oven 240 to dehydrate a monolayered food product on a belt having a width. The dehydration profile of the food products along the width of the belt may differ for a number of reasons including, but not limited to, variable pre-form or food product thickness (a thinner pre-form will dehydrate more quickly than a thicker pre-form), variation of burner firing along the width or length of the impingement oven, variation in air velocity contacting the pre-forms along the width or length of the oven, etc. Consequently, the possibility exists that some food products in a given batch can have higher levels of acrylamide than the average for that batch and can increase the average level of acrylamide for that batch. Making food products having more consistent levels of acrylamide can help enhance control of the average acrylamide level in food products.

One way to enhance the measurement and subsequent control of acrylamide formation is by the use of wavelength emission data to provide a thermal image of the food products exiting an oven. In a thermal imager, the field of view is scanned in a two-dimensional raster and each point in the image plane is handled in the same way as a thermometer target point. The image data can be generated with the temperature of each point indicated on a density (grey) scale or a color temperature contour map. Similarly, a line scanning thermometer can measure a temperature profile across a target's surface.

Figure 3:
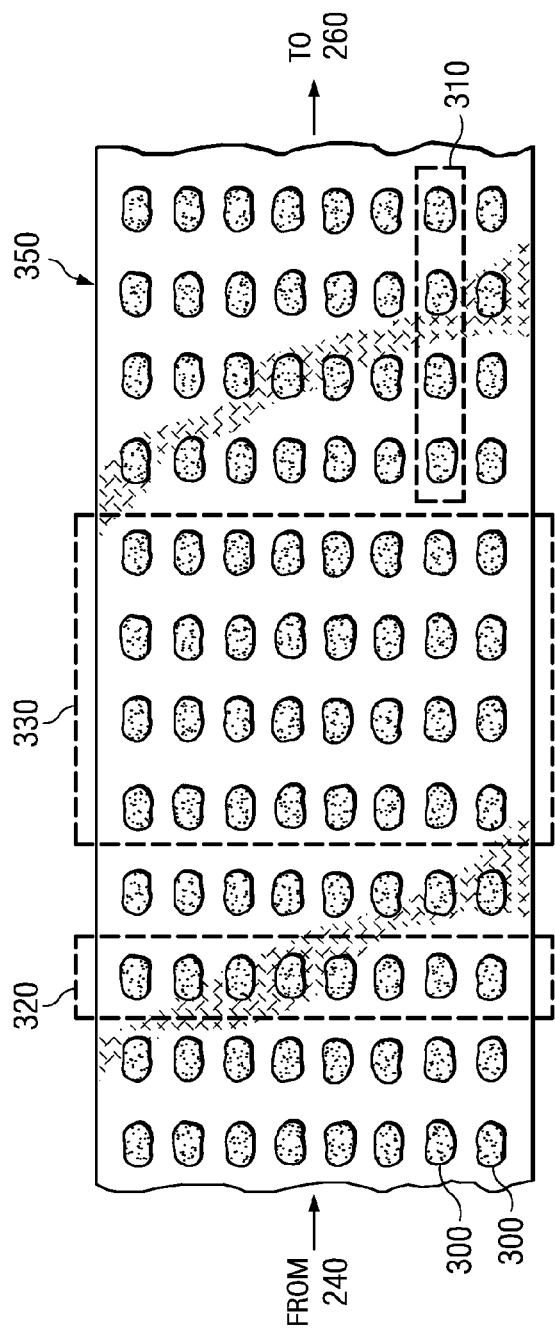
FIG. 3 is a partial, top view of the conveyor having discrete food pieces exiting the first oven depicted in FIG. 2.

FIG. 3 is a partial, top view of the conveyor 350 having discrete food pieces 300 exiting the first oven 240 depicted in FIG. 2. Referring to FIG. 3, pre-forms 300 exit the first oven 240 in a monolayer fashion. Here a mid-infrared camera 202 (as depicted in FIG. 2), can be used above the food product to gather wavelength emission data in the mid-infrared range (e.g., 3000 nm to about 10000 nm) to detect thermal gradients of food product exiting the oven 240. The thermal gradient can be measured longitudinally, for example, by taking a longitudinal snap shot 310 of chips at one time and measuring the temperature for each discrete food product in the longitudinal snap shot 310. Then, based on the distance between the measurements, a cooling rate of the food product as the food product exits an oven 240 can be derived.

In one embodiment, a transverse snapshot 320 can be taken to measure the temperature distribution across the width of the conveyor 350. In one embodiment, a larger snap shot 330 can be taken to assess both the transverse and longitudinal temperature distribution. Such image view 330 can ascertain temperature readings of that entire image view. Based on one or more of the temperature measurements provided from a thermal imaging array from the longitudinal snap shot 310, the transverse snap shot 320 and/or the larger snap shot 330, changes such as temperature, temperature gradients, etc. can be ascertained and this information can be used to make time, temperature or other adjustments to a unit operation such as the sheeter 220, the first oven 240 or the second oven 260 to adjust the level of acrylamide in the finished food product. For example, if the conveyor 350 temperature exiting the first oven 240 is the same across the width and the chip temperatures vary across the width, the sheeter gap along the width of the sheeter 220 can be adjusted to obtain a more consistent temperature to ensure the mass per unit area of food product is constant about the width. Similarly, if the conveyor 350 has a different temperature about the transverse width, meaning that one side of the belt is being preferentially heated more than the other side, it can mean that the oven is not firing correctly across the width. The oven heat profile may be adjusted by adjusting variables such as the oven damper, heat flux 242 (shown in FIG. 2) and other heat flow control devices within the oven 240.

The cooling rate information supplied from a longitudinal temperature profile can be used not only as a predictor of upstream conditions such as sheet thickness and upstream oven conditions, but the information can then be used to adjust the time/temperature conditions in the second oven 260. Thus, once measured, the cooling rate can also be used to adjust upstream, primary oven 240 variables (e.g., feed backward) or downstream, secondary oven 260 variables (e.g., feed forward). In one embodiment, the thermal image of a discrete food product can be time lagged to allow the same product to be measured at a precise time interval downstream making it possible to detect and correct underlying causes of moisture variability originating in either the raw material, preparation, or thermal processing step. For example, in one embodiment, a thermal image can be taken of the same dough pre-form at the first oven 240 inlet, at the first oven 240 outlet and at the second oven 260 outlet. Scanning NIR measurements made at the dough stage permits prediction of the transformation of the dough through the first oven by building multivariate models that relate the inlet variables measured using NIR techniques to output product attributes (moisture, color, acrylamide, etc) measured (using lab or on-line instruments) at the outlet of the first oven. The models are built using multivariate statistical software tools like those provided by Simca P+, Umetrics, Kinnelon, N.J. Other software tools available from companies such as MiniTab of State College, Pa., USA, and JMP software, a division of SAS in Cary, N.C. The process uses PLS techniques to create correlation models based on results derived by conducting designed experiments that establish the processing envelope of the process required to establish desired product attributes. These correlation models can then be used to make a multivariate model. The multivariate model can be used to predict outcomes at the exit of the first oven 240, based on the input NIR scans and the operating conditions in the first oven 240, and the predicted result is used to feed forward to the input of the second oven 260 to compensate for the relatively long residence time (6-10 minutes) in the secondary oven 260 as compared to the relatively short (e.g., 35-70 second) residence time in the first oven 240. In one embodiment, this can be important because the actual conditions in the first oven 240 cannot be physically changed as quickly as the raw material properties changes. This is driven by the relatively short period of time that the product spends in the first oven 240 (35-70 seconds) as compared to the response time of the oven conditions (3-15 minutes). Thus, it is possible to feed changes from an inferred moisture forward to the dehydration step 260 to achieve desired moistures and temperatures at the second oven 260 outlet. For example, the first oven 240 can be adjusted to drive the moisture content closer to a desired set point and the second oven 260 can be adjusted to compensate for the higher moisture content. An advantage of using a thermal imaging array is that visible browning is not required as evidence of conditions favoring acrylamide formation. The present invention thereby provides the ability to identify acrylamide formation characteristics and to take action to lower the acrylamide formation in a finished food product. The invention also provides a way to detect and correct imbalances in the upstream process equipment and/or systems that result in different product temperatures at the exit of the unit operation.

In one embodiment, thermal imaging devices can be placed to observe food product temperatures of pre-forms at locations within the drying oven 240 260. In one embodiment, thermal imaging devices are placed immediately prior to the exit of an oven 240 260 to assure that food product temperatures conducive to excessive levels (which can be determined based on the tolerance level of acrylamide level in the food) of acrylamide formation are not exceeded. For example, the temperature of the monolayered product or bedded product can be integrated as a constraint in a Constrained Model Predictive Control ("CMPC") Strategy employed to manage these processes. The CMPC strategy can leverage the previously described multivariate model of the first oven in conjunction with a similar model that has been developed for the second oven. The product thermal information will be integrated into the models as a "constraint" that adjusts the action taken by the different control variables (residence time, temperature, air fan speeds/velocity, control dampers, gas flow rates, electrical currents and/or electric potential/voltage in the case of an electric oven, and etc) so as to limit the product temperature while simultaneously achieving desired product color development and product moisture content. An additional overall multivariate control model will be built to oversee and optimize the combined action of these two constrained multivariate model predictive controllers.

Figure 4:
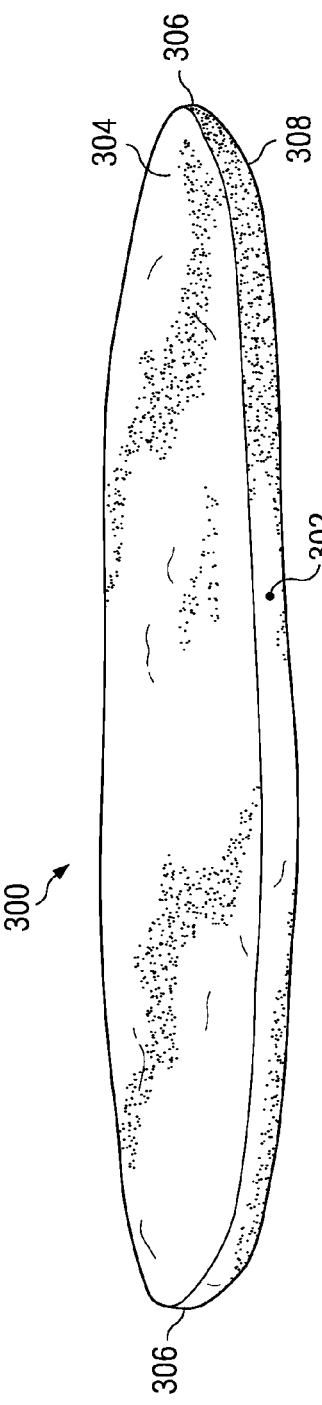
FIG. 4 is a perspective view of a food piece in accordance with one embodiment of the present invention.

In one embodiment, thermal imaging is used to observe the heat flux density of each food piece. FIG. 4 is a perspective view of a food piece in accordance with one embodiment of the present invention. Although the overall product moisture content of the pre-form exiting the first oven 240 is relatively high (e.g., between about 9% and about 12%), there is a moisture gradient from the pre-form center 302 outward to the pre-form top 304 and pre-form bottom 308. There is more moisture in the pre-form center 302 than on the pre-form top 304 and the pre-form bottom 308. Free moisture can help keep the food product temperature at 100° C., however, as free moisture is lost through evaporation, the temperature of the pre-form begins to rise. Free moisture is removed at a faster rate at the pre-form top 304 and pre-form bottom 308 than in the center 302 of the pre-form. Free moisture is removed at the highest rate at the outer peripheral edges 306 of the pre-form. Consequently, acrylamide can form on the outer edges 306 of the pre-form and along the top and bottom of the pre-form even when the pre-form as a whole has relatively high moisture rates.

One advantage provided by the present invention is that by observing the thermal gradient between the center and edges of the chip using IR Thermography edge browning which has been demonstrated to be very high (3000 to 7000 ppb) in acrylamide can be predicted and eliminated. The first oven control variables (gas flow, temperature, air velocity, dampers, and/or speed) can be managed to minimize both the temperature gradient and the overall edge temperature, thereby eliminating formation of edge browning and the high acrylamide region of the chips. The principle here is that in a flux (in this case heat) field, the flux density is concentrated at edges, corners, and boundaries. Sharp, pinch cut, edges and corners like the edges of our chips which are relatively large, flat, thin bodies experience very high flux densities at the edges.

In one embodiment, in the first zone of the first oven, process temperatures are in the range of 575-600° F., five of the remaining seven zones have temperatures above 500° F. and the remaining zones have temperatures between about 350° F. and about 400° F. This creates a high intensity heat field and the presence of sharp, thin, edges. By effectively measuring the consequence of exposure of each piece, using thermographic imaging, the extent of excess edge drying, and thereby browning, that results from changes in, for example, potato flake lot composition can be reduced. Because lots of potato flake typically last on the order of days and exhibit fairly consistent behavior in terms of edge browning, first oven process conditions can be adjusted to address edge browning.

Another way to enhance or control the level of acrylamide formation in a food product is to collect wavelength emission data in the color range for a number of samples (e.g., samples 1-10) and then to correlate this wavelength emission data with analytical laboratory levels of acrylamide and/or acrylamide pre-cursors for these same samples (e.g., samples 1-10). U.S. patent application Ser. No. 10/832,676, the entirety of which is hereby incorporated by reference, discloses a method for extracting feature information from product images using multivariate image analysis to develop predictive models for feature content and distribution on the imaged product.

In one embodiment, a fast real time acrylamide level is calculated at a first location (e.g. oven or fryer exit) and a second real time acrylamide level is calculated at a second location (e.g. oven or fryer inlet). The first real time acrylamide level can be averaged with the second real time acrylamide level to obtain an overall real time acrylamide level to enhance the accuracy. The average can be weighted if desired. Consequently, in one embodiment, a plurality of real time acrylamide levels can be used as a basis for adjusting one or more process variables at one or more unit operations to result in a robust acrylamide monitoring system. For example, the time and temperature of exposure of a food product in the fryer can be optimized so as to reduce, lower and/or minimize the level of defects in the finished food product. For example, the paddle wheel speed can be adjusted to adjust the residence time in the fryer and/or the hot oil temperature can be adjusted. Other process levels that can be adjusted include, but are not limited to, oil flow rate into the fryer, the oil level in the fryer, the submerger speed, the take out conveyor speed, the inlet oil temperature, and the product feed rate. One advantage of such embodiment is that it permits the creation of a multivariate model that permits a way to analyze how various variables such as heat load, heat flux, cooling rates, compositional analysis, etc. interact together and can provide unforeseen automated ways to not only reduce but to minimize the level of acrylamide in food products automatically.

EXAMPLE

Baked Potato Chip

An actual example of the method for monitoring the real-time acrylamide level based on measurements of the wavelength emission data is provided below for baked potato crisps. Also provided is a prophetic example of an automated control strategy using the real-time acrylamide data for baked potato crisps.

A potato flake based dough was sheeted and cut into preforms and routed in a monolayer fashion to a gas-fired impingement oven for 50 to 60 seconds having an oven temperatures of about 600° F. to about 350° F. The chips exiting the impingement oven had a moisture content of between about 9.5% and about 10.5% by weight. The potato chips were then cured at ambient or cooled temperatures for between 5 seconds and 30 seconds prior to being routed to a multi-zone oven having temperatures of between about 220° F. and about 290° F. for about 7 to about 10 minutes. At the exit, the baked potato chips had a moisture content of between about 1.2% and about 2.5% by weight. The near infrared wavelength emission reflectance data was collected from 8 samples under various test conditions when the chips were about 96 inches from the oven outlet with a near infrared unit from Unity Scientific of Columbia, Md. For example, various test conditions under which the samples were collected refers to samples collected at target finished product moisture set points between 1.1% and 3.0% derived by controlling final dryer zone temperatures, fan speeds, and/or residence times. The reflectance range of 1200 nm to 2400 nm was collected and recorded. The near infrared spectral wavelength data for each sample of chip was stored in a Microsoft Excel spreadsheet. The same area of these same chips were then analyzed for an acrylamide level in an in-house analytical laboratory by GC-MS.

A Principal Component Analysis ("PCA") and Projection of Latent Structures (PLS) analysis was performed on the data from the NIR spectral wavelength data using Simca P+ software provided by Umetrics Inc, Kinnelon, N.J. to evaluate the NIR spectra. To assure that the NIR measured acrylamide content of the samples was not merely a reflection of finished product moisture content, the near infrared spectra related to moisture content (e.g., wavelengths range 1400 nm to 1450 nm and 1900 nm to 1950 nm) was removed and the remaining wavelength data was correlated with the acrylamide levels corresponding to the laboratory analysis of acrylamide levels. Consequently, in one embodiment, the correlation of the off-line acrylamide level (e.g., acrylamide level determined by an analytical laboratory) and the on-line acrylamide level occurs in the near infrared spectra of between about 1200 nm and about 2400 nm while omitting bands of between 1400 nm to 1450 nm and 1900 nm to about 1950 nm. Those having ordinary skill in the art understand PCA/PLS and the intricacies of analysis. Consequently, the operation of the commercial software need not be discussed in great detail. However, the data produced by the software will be discussed.

Figure 6:
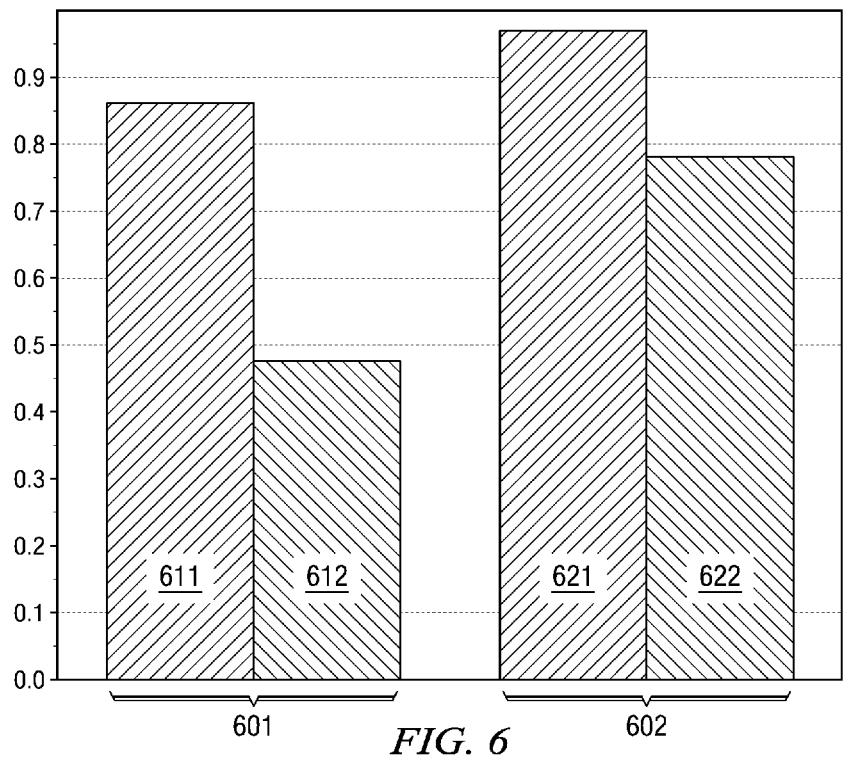
FIG. 6 is a graphical representation of the PCA/PLS analysis performed on the NIR wavelength emission data in accordance with one embodiment of the present invention.

FIG. 6 is a graphical representation of the PCA/PLS analysis performed on the NIR wavelength emission data. Shown in FIG. 6 is a Component One 601 and Component Two 602. Component One 601 further has an r-squared value 611 and a q-squared value 612. Similarly, Component Two 602 has an r-squared value 621 and a q-squared value 622. Those having ordinary skill in the art will understand that Component Two 602 is rotated in relation Component One 601 to minimize the variability. The r-squared values 611 621 is the squared multiple correlation coefficient. The q-squared values 612 622 represent the predictability of the model. The fact that the r-squared 621 and q-squared 622 values for Component Two 602 are higher than the respective r-squared 611 and q-squared 612 values for Component One 601 means that the model is becoming more accurate with the second component 602.

Using the first and second principal components calculated in FIG. 6, a model is built in the multivariate space to extract the information from the wavelength reflectance data. The wavelength reflectance data is processed through a first derivative function to enhance compliance of the model. The PLS methodology was then applied, using the same Simca P+ software, for 20 iterations to create a transformed wavelength emission data or transformed spectra to produce a first derivative coefficient at each desired wavelength. As used herein, the term "transformed spectra" is synonymous with the term "transformed wavelength emission data."

When the first derivative coefficients were used to create an algorithm correlating acrylamide levels with the first derivative coefficients at specific wavelengths outside the wavelength emission bands of 1400 nm to 1450 nm and 1900 nm to 1950 nm, the algorithm produced had a root means squared error or r-square value of 0.97. Thus, a real time and accurate predictor of acrylamide was determined with an algebraic equation using the specific wavelength regions revealed by the food products. Thus, NIR readings can now be used outside of this process to provide a real time acrylamide level of food products on a manufacturing operation. The correlation, as measured by r-squared, between the predicted acrylamide values based on wavelength emission data and the off-line acrylamide level is preferably greater than about 0.95.

Figure 7:
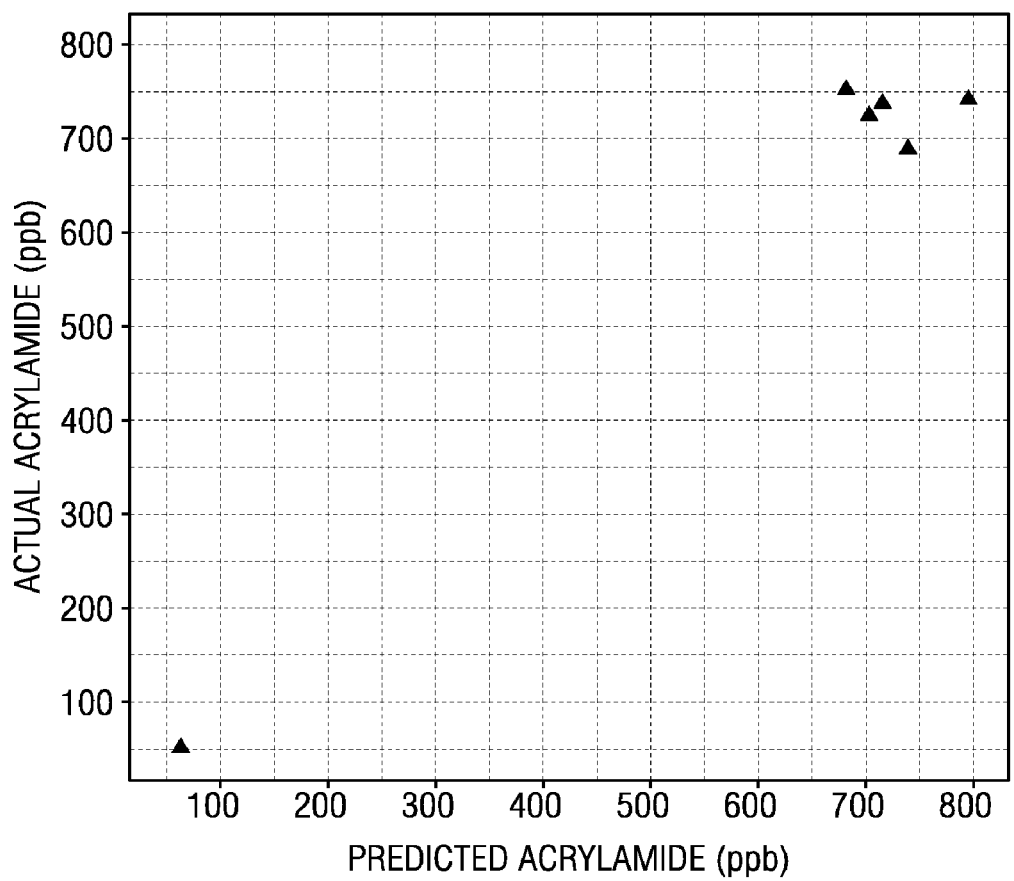
FIG. 7 is a graphical depiction of actual and predicted acrylamide levels in a baked food product in accordance with one embodiment of the present invention.

FIG. 7 is a graphical depiction of actual and predicted acrylamide levels in a baked food product using the above algorithm. As shown by the data in FIG. 7, the present invention provides an accurate real-time predictor of acrylamide levels not previously available in the art. In one embodiment, the accuracy of the model is enhanced because the wavelength emission data related to water molecules is removed from the model.

The real-time acrylamide data produced by the methods described above can be provided to operators to manually make manual adjustments to the process to lower the acrylamide level and/or an advanced multivariate control strategy to automatically lower the level of acrylamide in a food product. For example, the predicted real-time acrylamide levels can then be modeled with other measured and recorded product measurements at various process locations. Other measured and recorded product variables in a baked food product can include, but are not limited to, the first oven zone temperatures, first oven zone energy inputs (gas flow rates), first oven residence time, first oven zone air flow distribution, sheeted product thickness/uniformity (across the web), first oven residence time, first oven outlet product temperature, first oven outlet product temperature gradient, first oven outlet product moisture, first oven outlet product acrylamide, second oven zone temperatures, second oven zone residence times (bedding), second oven air flows (plenum pressures and fan speeds) by damper positions to balance air flow through the product bed, second oven product temperature in each zone, second oven outlet product moisture, second oven outlet product acrylamide, second oven outlet product temperature, and the second oven outlet product color.

Algorithms can similarly be constructed for acrylamide pre-cursors for the real-time monitoring of acrylamide precursors. The predicted real-time acrylamide and/or acrylamide pre-cursors levels and the measured and recorded product variables can be integrated into a Constrained Model Predictive Control ("CMPC") Strategy employed to manage the final acrylamide level of a food product. The predicted real-time acrylamide levels or real-time acrylamide pre-cursor levels can be integrated into the models as a "constraint" that adjusts the action taken by the different control variables (residence time, temperature, air fan speeds/velocity, control dampers, gas flow rates, and etc) so as to limit the product temperature while simultaneously achieving desired product color development and product moisture content. Armed with this disclosure, one having ordinary skill in the art can build an additional overall Multivariate Control model to oversee and optimize the combined action of two or more constrained multivariate model predictive controllers.

The above example can be applied to other food manufacturing process lines, such as a fried potato chip line. The wavelength emission data for fried potato chips exiting the fryer can be measured. In one embodiment, the wavelength emission data is recorded after defective potato slices have been removed. Potato slices with defects have been found to be linked with higher levels of acrylamide when fried in hot oil (e.g., fried in oil having an oil temperature of greater than about 280° F.) than potato slices having no potato defects. A potato slice having no defects is a slice having an evenly golden color on its entire surface area after frying. Potato defects are well known to those skilled in the art and such defects include, but are not limited to, zebra, dry rot, scab, hollow heart, greening, blacklegs, sprouting, bruises, leaf roll and sugar defects. Removal of such defective potato slices can be achieved by placing a potato defect detector downstream of the fryer to remove defective potato slices prior to the packaging process. A sorting apparatus, such as an 40 Optyx 6000 available from Key Technology, Walla Walla, Wash., US, can be used.

The Visible and/or NIR wavelength emission data can be correlated to calculate a real time acrylamide level based upon the wavelength emission data as described above. The real time acrylamide level in the food product is, in one embodiment, averaged over a period of about 10 to about 180 seconds prior to reporting the real time acrylamide level to an operator by way of an operator interface device, or to an automated control system. The averaging of many spectral scans provides the benefit of large numbers in establishing the average acrylamide content of the product. Individual scans can be completed in from about 0.100 to 3.0 seconds depending on the capability of the scanning Visible/NIR instrument used. In one embodiment, scan times are set to 1 second. Such averaging can also occur in baked products as well and further extends to all forms of on-line scanning instruments (NIR, Visible, Thermographic, etc). Scan time requirements vary depending on both the technology deployed in the scanning instrument and the requirements of the process in terms of line speed. High speed process lines require high speed scanners in order to provide clear, unblurred, images that can be evaluated; whereas, slow moving process lines can use less expensive slower scanning instruments.

Acrylamide levels can also be predicted in real-time from multivariate models of on line measurements of critical process variables that are precursors of acrylamide development. The predicted real-time acrylamide levels and the measured and recorded product variables can be integrated into a Constrained Model Predictive Control ("CMPC") Strategy employed to manage the final acrylamide level of a food product. The CMPC strategy can leverage a Multivariate model of the fryer. The predicted real-time acrylamide levels and/or predicted real-time acrylamide pre-cursor levels can be integrated into the models as a "constraint" that adjusts the action taken by the different control variables such as the submerger speed, fryer temperature, paddle wheel speed, slice distribution into the fryer, individual zone oil flow splits, total oil flow rate, oil level in the fryer, the make-up oil flow, the heat exchanger input energy (steam, gas, thermal fluid, electricity, oil, coal, etc), the fryer pan slope, the take out conveyor speed and food product pretreatments such as the temperature, residence time and concentration level of acid baths, calcium chloride baths, etc. so as to limit the product temperature while simultaneously achieving desired product color development and product moisture content.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

I claim:

1. A method for measuring the level of acrylamide in a food product, said method comprising the steps of:
   a) collecting wavelength emission data for a plurality of food products;
   b) testing said food products off-line for an off-line acrylamide level; and
   c) correlating said off-line acrylamide level with said wavelength emission data such that a real time acrylamide level is calculated from said wavelength emission data, wherein said correlation occurs by utilizing wavelength emission data between about 1200 nm and about 2400 nm while omitting wavelength emission data of between about 1400 nm to about 1450 nm and about 1900 nm to about 1950 nm.

2. The method of claim 1 further comprising the step of:
   d) adjusting one or more process variables at a unit operation to lower the real time level of acrylamide in said food product.

3. The method of claim 2 wherein said unit operation comprises an oven and wherein said process variable comprises an oven temperature.

4. The method of claim 2 wherein said unit operation comprises an oven and wherein said process variable comprises a food product residence time.

5. The method of claim 2 wherein said unit operation comprises an air velocity.

6. The method of claim 2 wherein said unit operation comprises a gas flow rate.

7. The method of claim 2 wherein said unit operation comprises an electrical current.

8. The method of claim 2 wherein said unit operation comprises a voltage.

9. The method of claim 1 wherein said collecting at step a) occurs at the exit of a unit operation.

10. The method of claim 9 wherein said unit operation comprises a dehydrator.

11. The method of claim 9 wherein said unit operation comprises a first oven.

12. The method of claim 2 wherein said unit operation comprises a fryer.

13. The method of claim 1 wherein said collecting at step a) comprises collecting data at the exit of at least two unit operations.

14. The method of claim 13 wherein said correlating at step c) comprises a multivariate analysis.

15. The method of claim 1 wherein said correlation comprises an r-squared of greater than about 0.90.

16. The method of claim 2 wherein said unit operation comprises a fryer and wherein said process variable comprises an inlet oil temperature.

17. The method of claim 2 wherein said unit operation comprises a fryer and wherein said process variable comprises a paddle wheel speed.

18. The method of claim 2 wherein said unit operation comprises a fryer and wherein said process variable comprises a product feed rate.

19. The method of claim 2 wherein said unit operation comprises a fryer and wherein said process variable comprises an oil level.

* * * * *